United States Patent
Bae et al.

(10) Patent No.: US 7,771,361 B2
(45) Date of Patent: Aug. 10, 2010

(54) BLOOD PRESSURE MEASURING APPARATUS AND METHOD OF MEASURING BLOOD PRESSURE

(75) Inventors: Sang-kon Bae, Seongnam-si (KR); Kun-soo Shin, Seongnam-si (KR); Jong-pal Kim, Seoul (KR); Youn-ho Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 12/025,078

(22) Filed: Feb. 4, 2008

(65) Prior Publication Data

US 2009/0069698 A1    Mar. 12, 2009

(30) Foreign Application Priority Data

Sep. 6, 2007   (KR) .................. 10-2007-0090555

(51) Int. Cl.
*A61B 5/02* (2006.01)

(52) U.S. Cl. .............. 600/485; 600/481; 600/500; 600/504

(58) Field of Classification Search .......... 600/481–507
See application file for complete search history.

(56) References Cited

U.S. PATENT DOCUMENTS

| | | | | |
|---|---|---|---|---|
| 4,660,566 A | * | 4/1987 | Palti | 600/490 |
| 6,162,185 A | * | 12/2000 | Amano et al. | 600/557 |
| 6,210,340 B1 | * | 4/2001 | Amano et al. | 600/500 |
| 6,491,647 B1 | * | 12/2002 | Bridger et al. | 600/585 |
| 6,533,729 B1 | * | 3/2003 | Khair et al. | 600/503 |
| 6,676,600 B1 | * | 1/2004 | Conero et al. | 600/438 |
| 7,306,563 B2 | * | 12/2007 | Huang | 600/500 |
| 2002/0026121 A1 | * | 2/2002 | Kan | 600/500 |
| 2003/0139674 A1 | * | 7/2003 | Stergiopoulos et al. | 600/490 |
| 2008/0082004 A1 | * | 4/2008 | Banet et al. | 600/485 |
| 2008/0228089 A1 | * | 9/2008 | Cho et al. | 600/485 |

* cited by examiner

*Primary Examiner*—Patricia C Mallari
*Assistant Examiner*—Karen E Toth
(74) *Attorney, Agent, or Firm*—Sughrue Mion, PLLC

(57) ABSTRACT

Provided is a blood pressure measuring apparatus and a method of measuring blood pressure. The blood pressure measuring apparatus includes a plurality of blood pressure measuring units disposed on a substrate, a plurality of optical sensors disposed on the substrate to correspond to the blood pressure measuring units, and a control unit that measures blood pressure by analyzing signals received from the optical sensors and the blood pressure measuring units, wherein each of the blood pressure measuring units comprises a plurality of blood pressure sensors.

4 Claims, 6 Drawing Sheets

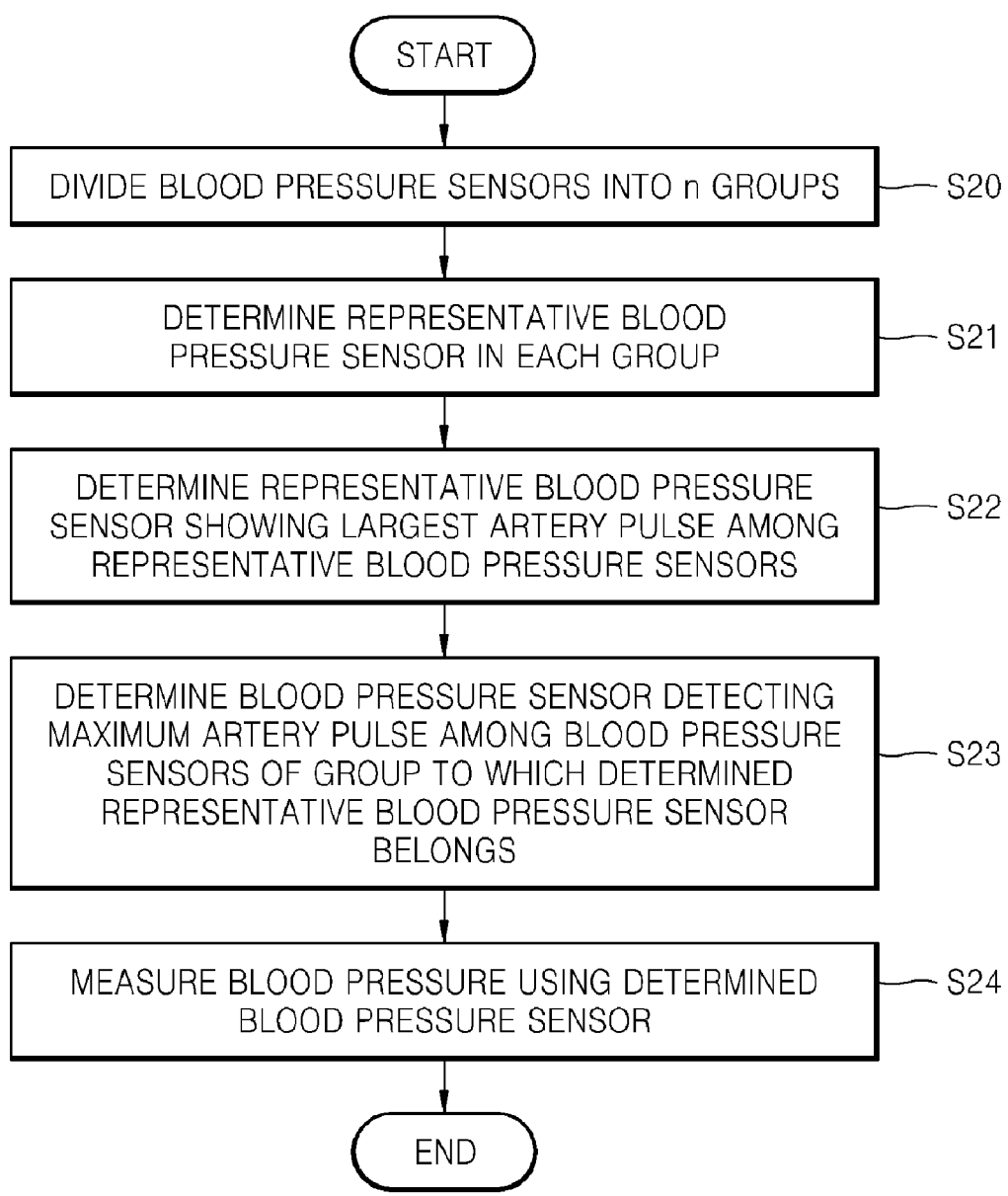

BLOOD PRESSURE MEASURING APPARATUS AND METHOD OF MEASURING BLOOD PRESSURE

CROSS-REFERENCE TO RELATED PATENT APPLICATION

This application claims the benefit of Korean Patent Application No. 10-2007-0090555, filed on Sep. 6, 2007, in the Korean Intellectual Property Office, the disclosure of which is incorporated herein in its entirety by reference.

BACKGROUND OF THE INVENTION

1. Field of the Invention

The present invention relates to a blood pressure measuring apparatus and a method of measuring blood pressure, and more particularly, to a blood pressure measuring apparatus used for a tonometry test method and a method of measuring blood pressure.

2. Description of the Related Art

Blood pressure is classified into arterial blood pressure, capillary blood pressure, and vein blood pressure. Generally, blood pressure indicates the arterial blood pressure that varies according to heartbeat.

In a tonometry test method, which is one of the methods of non-invasively measuring blood pressure, blood pressure is measured by pressing a pressure sensor in a direction of a radial artery after locating the pressure sensor on the radial artery of the wrist. At this point, a sensing unit of the pressure sensor deforms due to blood pressure, and thus, the blood pressure is measured by measuring the deformation of the sensing unit.

The pressure sensor for measuring blood pressure outputs a pressure value as an electrical signal, and the electrical signal is processed so as to be read as blood pressure. The pressure sensor and a signal processing system constitute a blood pressure measuring system.

When blood pressure is measured from the radial artery of the wrist, which is a measuring point, and one pressure sensor is used, the pressure sensor must be correctly located on the radial artery to accurately measure blood pressure. For this purpose, the maximum blood pressure is measured by moving the pressure sensor using an actuator. However, in this case, since the actuator is necessary, the realization of a compact blood pressure measuring apparatus is difficult.

Instead of using the actuator, a plurality of pressure sensors may be used. In this case, a sensor signal detected from a position where a biomedical signal is the largest among several sensor signals may be used. This method is advantageous for realizing a small and lightweight blood pressure measuring apparatus since an actuator is unnecessary. Theoretically, if small pressure sensors are disposed in a row, at least one pressure sensor is located on a correct location of the radial artery.

However, if the number of sensors is low due to an area of the pressure sensor, the sensitivity of finding the position of radial artery of the wrist is reduced, and thus, an accurate measurement of the blood pressure is difficult.

Also, if the number of sensors is increased by reducing sensor areas, it will take time to find the position of the radial artery of the wrist by calculating the amplitude of a pulse wave of each of the sensors.

SUMMARY OF THE INVENTION

To address the above and/or other problems, the present invention provides a blood pressure measuring apparatus that has increased sensitivity of finding the position of the radial artery and may reduce the time required for finding the radial artery, and a method of measuring blood pressure.

According to an aspect of the present invention, there is provided a blood pressure measuring apparatus comprising: a plurality of blood pressure measuring units disposed on a substrate; a plurality of optical sensors disposed on the substrate to correspond to the blood pressure measuring units; and a control unit that measures blood pressure by analyzing signals received from the optical sensors and the blood pressure measuring units, wherein each of the blood pressure measuring units comprises a plurality of blood pressure sensors.

The substrate may be a flexible printed circuit board on which wires electrically connected to the blood pressure sensors and the optical sensors are formed.

The blood pressure sensor may be a piezoresistor.

The optical sensor may comprise a light emitting unit and a light receiving unit, wherein the light emitting unit and the light receiving unit are respectively disposed on both sides of the corresponding blood pressure measuring unit.

According to an aspect of the present invention, there is provided a method of measuring blood pressure using a blood pressure measuring apparatus that comprises: a plurality of blood pressure measuring units, each comprising a plurality of blood pressure sensors on a substrate; a plurality of optical sensors disposed on the substrate to correspond to the blood pressure measuring units; and a control unit that measures blood pressure by analyzing signals received from the optical sensors and the blood pressure measuring units, the method comprising: (a) measuring an optical signal according to each of the optical sensors by emitting and receiving light from the optical sensors; (b) measuring an artery pulse according to blood pressure using the blood pressure sensors of the blood pressure measuring unit that correspond to the optical sensor showing the largest variation of the optical signal; (c) determining the blood pressure sensor that shows the largest artery pulse; and (d) measuring blood pressure using the determined blood pressure sensor.

According to another aspect of the present invention, there is provided a method of measuring blood pressure comprising: (a) dividing a plurality of blood pressure sensors disposed in a row on a substrate into n groups, each group comprising a plurality of blood pressure sensors; (b) determining a representative blood pressure sensor of the blood pressure sensors in each of the blood pressure sensor groups; (c) determining a blood pressure sensor group that measures the maximum artery pulse by comparing the artery pulses measured by the representative blood pressure sensors; (d) determining the blood pressure sensor that detects the maximum artery pulse by comparing the artery pulses measured by the blood pressure sensor group to which the determined representative blood pressure sensor belongs; and (e) measuring blood pressure using the determined blood pressure sensor.

BRIEF DESCRIPTION OF THE DRAWINGS

The above and other features and advantages of the present invention will become more apparent by describing in detail exemplary embodiments thereof with reference to the attached drawings in which:

FIG. 7 is a flow chart showing a method of measuring blood pressure according to another embodiment of the present invention.

DETAILED DESCRIPTION OF THE INVENTION

The present invention will now be described more fully with reference to the accompanying drawings in which exemplary embodiments of the invention are shown.

Figure 1:
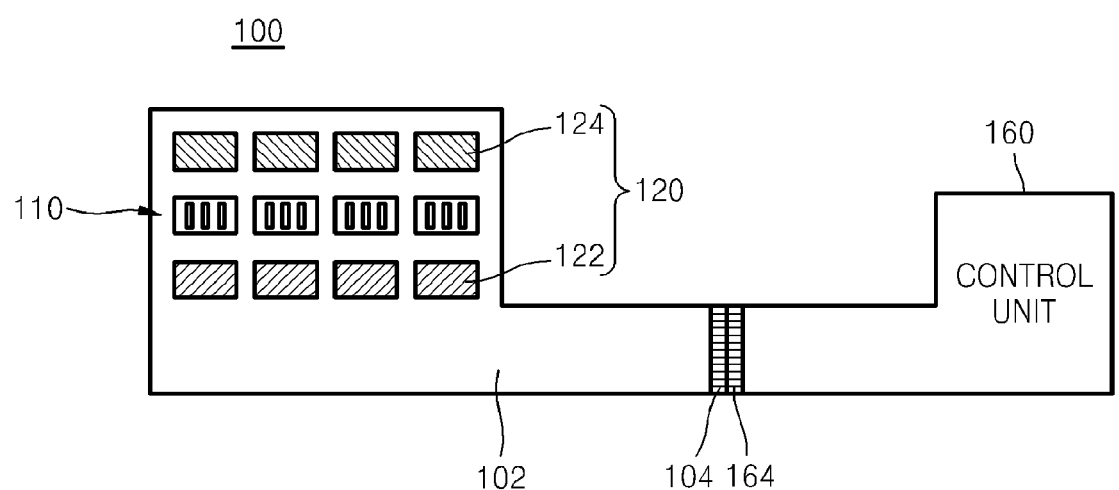
FIG. 1 is a schematic plan view of a blood pressure measuring apparatus according to an embodiment of the present invention.

FIG. 1 is a schematic plan view of a blood pressure measuring apparatus 100 according to an embodiment of the present invention.

Referring to FIG. 1, the blood pressure measuring apparatus 100 includes a plurality of blood pressure measuring units 110, a plurality of optical sensors 120 disposed on both sides of the blood pressure measuring units 110, and a control unit 160 that is connected to the blood pressure measuring units 110 and the optical sensors 120 to read blood pressure by analyzing data measured by the blood pressure measuring units 110. The blood pressure measuring units 110 and the optical sensors 120 may be formed on a flexible printed circuit board 102 in which predetermined wires (not shown) are printed. The control unit 160 may be electrically connected to a connector 104, to which the wires are connected, through a connector 164 of the control unit 160.

Each of the blood pressure measuring units 110 includes a plurality of blood sensors and wires and electrode pads connected to the blood sensors. The electrode pads are electrically connected to the wires printed in advance on the flexible printed circuit board 102. For convenience, in FIG. 1, each of the blood pressure measuring units 110 includes three blood sensors, but the present invention is not limited thereto.

Figure 2:
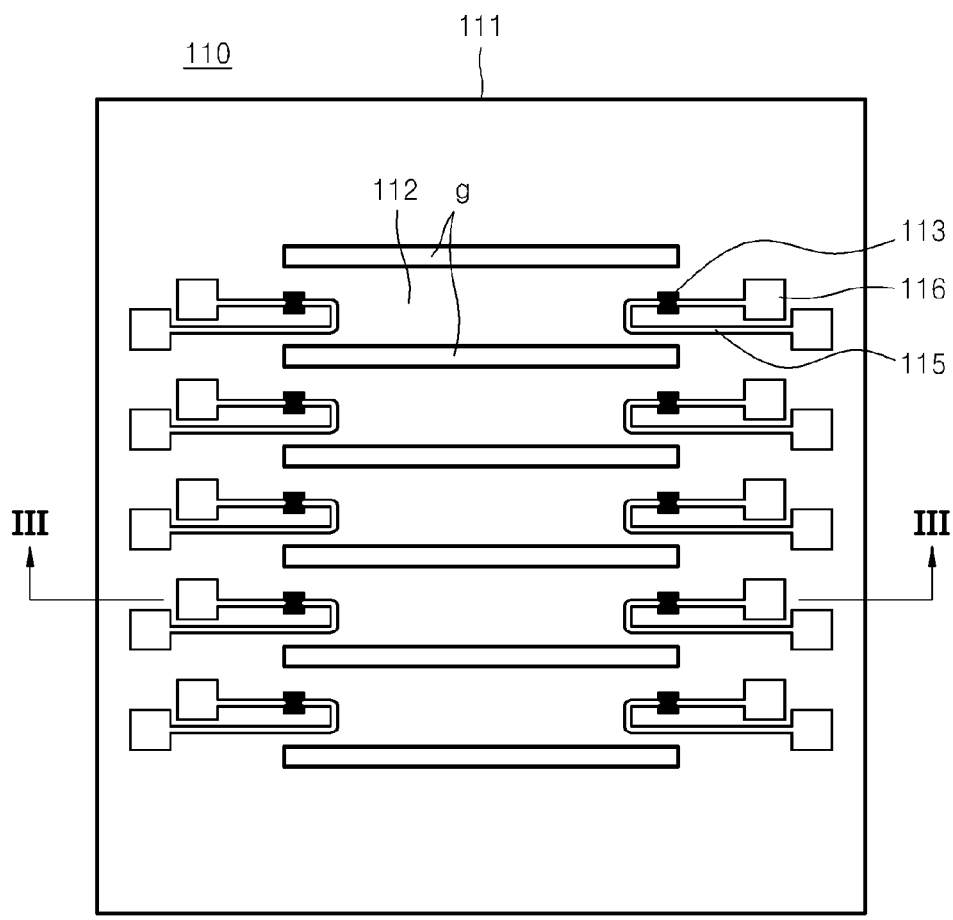
FIG. 2 is a plan view of a blood pressure measuring unit of a blood pressure measuring apparatus according to an embodiment of the present invention.
Figure 3:
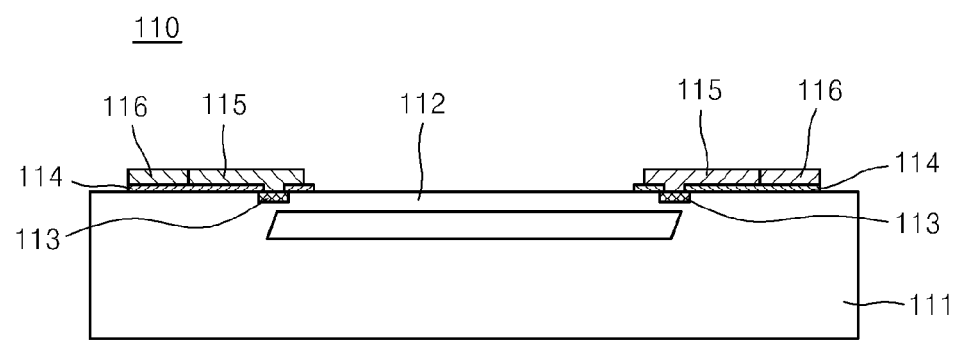
FIG. 3 is a cross-sectional view taken along line III-III of FIG. 2, according to an embodiment of the present invention.

FIG. 2 is a plan view of a blood pressure measuring unit 110 of the blood pressure measuring apparatus 100 according to an embodiment of the present invention. FIG. 3 is a cross-sectional view taken along line III-III of FIG. 2.

Referring to FIGS. 2 and 3, five both-ends supported bars 112 are arranged parallel to each other on a substrate 111. A plurality of piezoresistors 113, which are blood pressure sensors, are respectively placed on both ends of each of the both-ends supported bars 112. The substrate 111 may be an n-type single crystalline silicon substrate, and the piezoresistors 113 may be p-type regions in which boron is implanted. Wires 115, for example, Au wires, and electrode pads 116 are connected to both sides of the piezoresistors 113. Gaps g between the both-ends supported bars 112 and between the both-ends supported bar 112 and the substrate 111 may be formed to have a length of few micrometers or less. Insulating layers 114 are formed under the wires 115 and the electrode pads 116.

Each of the optical sensors 120 includes a light emitting unit 122 and a light receiving unit 124. The light emitting unit 122 may be a light emitting diode, preferably, an infrared ray emitting diode that emits infrared rays with a wavelength of, for example, 940 nm. The light receiving unit 124 may be a photo detector. The light emitting unit 122 and the light receiving unit 124 are respectively disposed on both sides of the corresponding blood pressure measuring unit 110, and are disposed parallel to the radial artery during detecting blood pressure. The light emitting unit 122 emits infrared rays, and there is a minimum optical reflection where the radial artery is located.

Figure 4:
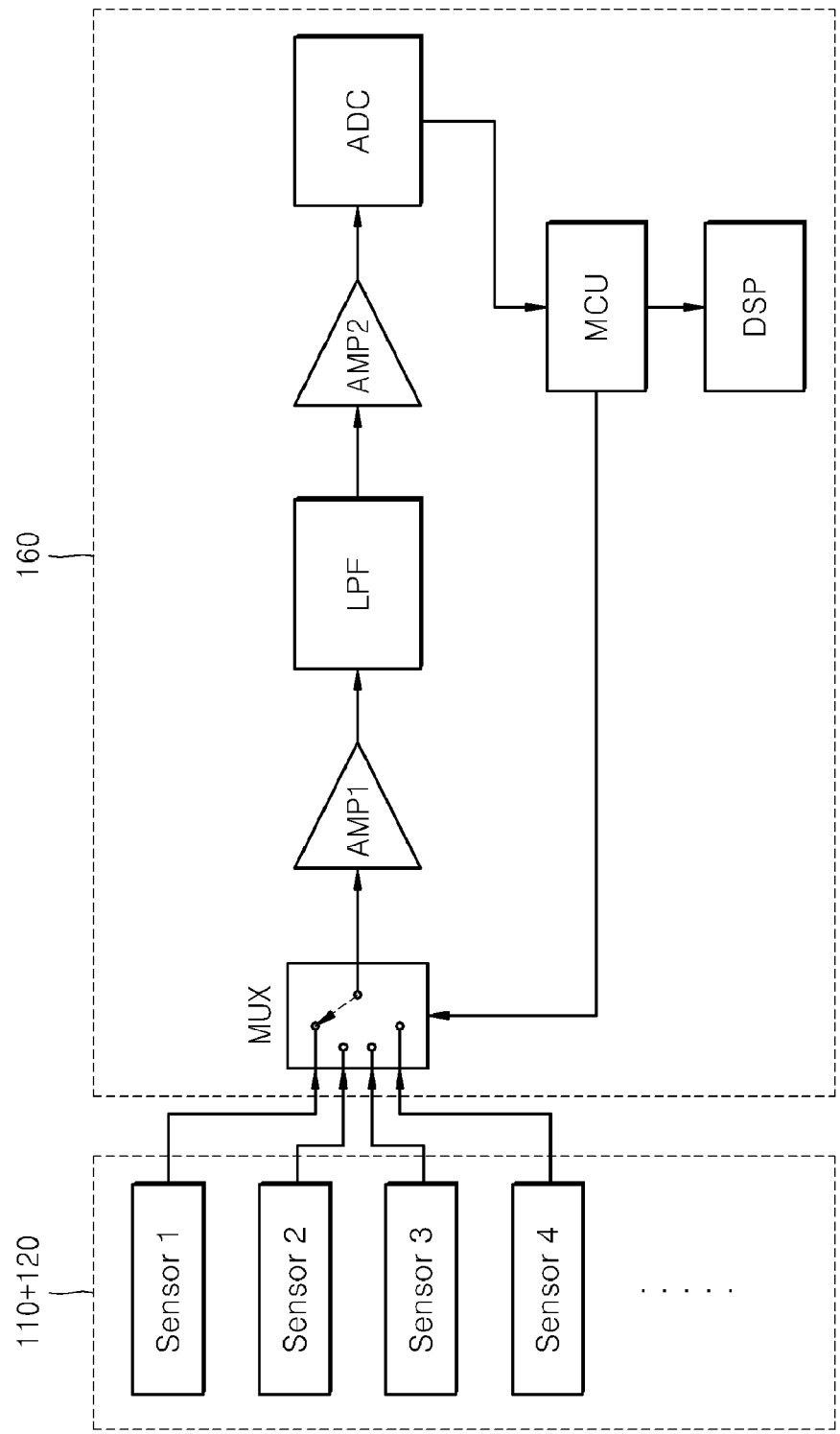
FIG. 4 is a block diagram showing a configuration of a control unit of a blood pressure measuring apparatus according to an embodiment of the present invention.

FIG. 4 is a block diagram showing a configuration of the control unit 160 of the blood pressure measuring apparatus 100 according to an embodiment of the present invention.

Referring to FIG. 4, the control unit 160 may include a multiplex MUX, a first amplifier AMP1, a low pass filter LPF, a second amplifier AMP2, an analogue-digital converter ADC, a main control unit MCU, and a display unit DSP.

The multiplex MUX is connected to the blood pressure sensors (piezoresistors) 113 and the optical sensors 120 of the blood pressure measuring units 110 to receive electrical signals from the blood pressure sensors 113 and the optical sensors 120 selected by the main control unit MCU. The main control unit MCU may select the blood pressure sensors 113 and the optical sensors 120 to be used for measuring blood pressure, and may determine the blood pressure sensor 113 and the optical sensor 120 that outputs the largest signal according to the pressure of the radial artery.

The first amplifier AMP1 amplifies an electrical signal received from the blood pressure sensors 113 and the optical sensors 120. The low pass filter LPF removes high frequency noise. The second amplifier AMP2 re-amplifies the signal that has passed through the low pass filter LPF. The analogue-digital converter ADC transforms an inputted analogue signal to a digital signal and outputs it to the main control unit MCU. The main control unit MCU measures the magnitude of an arterial pulse from the inputted digital signal, and calculates the blood pressure from the arterial pulse. The main control unit MCU displays measured digital data on the display unit DSP.

Figure 5:
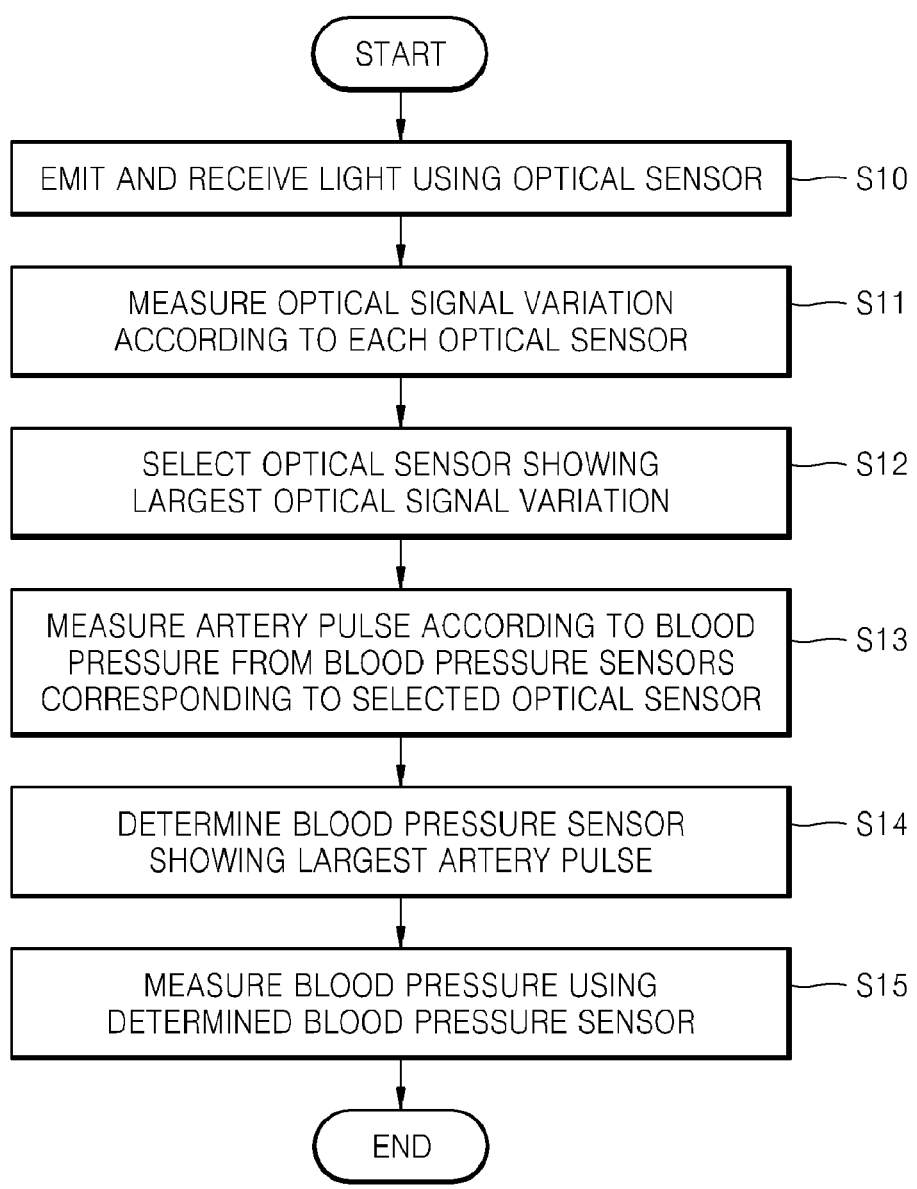
FIG. 5 is a flow chart showing a method of measuring blood pressure according to an embodiment of the present invention.

FIG. 5 is a flow chart showing a method of measuring blood pressure according to an embodiment of the present invention. The method of measuring blood pressure will now be described with reference to FIGS. 1 through 5.

Light is emitted from the light emitting units 122 of the optical sensors 120, and the optical signal is detected by the light receiving units 124 (S10). The main control unit MCU measures the variation of the optical signal received from the optical sensors 120 (S11).

Next, the optical sensor 120 that shows the largest variation (drop) of the optical signal is determined as being positioned on the radial artery (S12).

Next, the arterial pulse is measured using the blood pressure sensors 113 of the blood pressure measuring unit 110 corresponding to the determined optical sensor 120 (S13). For this purpose, a predetermined pressure is applied to the blood pressure sensors 113 towards the radial artery.

The main control unit MCU of the control unit 160 determines a blood pressure sensor 113 by which the largest arterial pulse of the inputted arterial pulses is measured (S14).

Next, blood pressure may be continuously measured using the blood pressure sensor 113 determined in the operation S14 (S15).

Prior to measuring the blood pressure using the determined blood pressure sensor 113, blood pressure may be calibrated. For this purpose, the blood pressure sensor 113 is pressed towards the radial artery by the pressure already known, and, a calibration may be performed by setting a relationship between blood pressure and voltage according to artery pulses.

In the method of measuring blood pressure according to the present embodiment, firstly, the position of a radial artery is detected using the optical sensor 120, and secondly, the blood pressure sensor 113 positioned on the radial artery is selected by analyzing artery pulses measured by blood pressure sensors 113 that belong to the blood pressure measuring unit 110 corresponding to the selected optical sensor 120. Thus, the number of artery pulse analysis for finding the blood pressure sensor 113 positioned on the radial artery is greatly reduced, and accordingly, the time required for finding the radial artery may be reduced, and also, the sensitivity of finding the radial artery may be increased since many blood pressure sensors 113 may be used.

Figure 6:
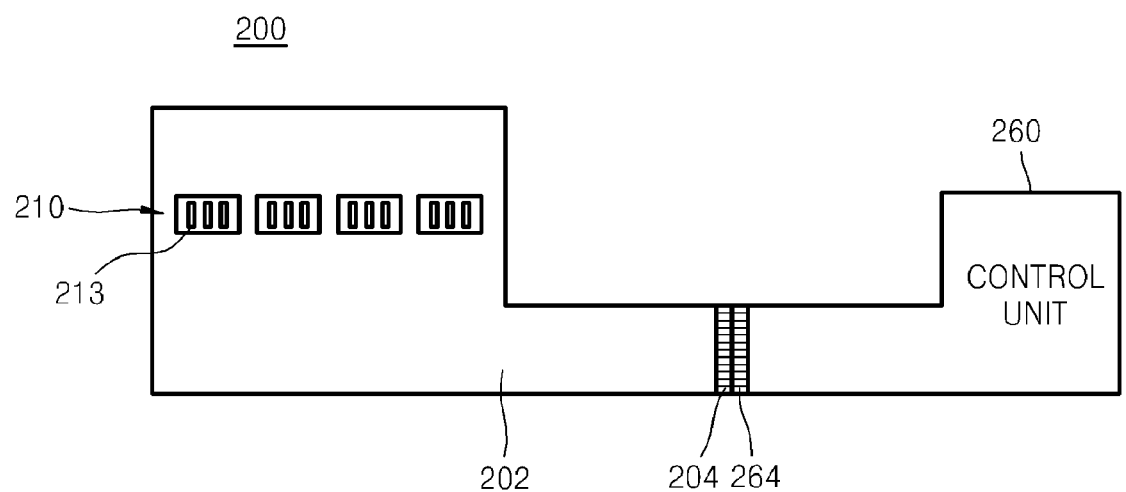
FIG. 6 is a plan view of a blood pressure measuring unit of a blood pressure measuring apparatus according to another embodiment of the present invention.

FIG. 6 is a plan view of a blood pressure measuring apparatus 200 according to another embodiment of the present invention.

Referring to FIG. 6, the blood pressure measuring apparatus 200 includes a plurality of blood pressure measuring units 210 and a control unit 260 connected to the blood pressure measuring units 210 to read blood pressure by analyzing measured data received from the blood pressure measuring units 210. The blood pressure measuring units 210 may be mounted on a flexible printed circuit board 202 on which predetermined wires (not shown) are printed. The blood pressure measuring units 210 and the control unit 260 may be electrically connected through the connection between a connector 204 which is connected to the wires of the blood pressure measuring units 210 and a connector 264 of the control unit 260.

Each of the blood pressure measuring units 210 includes a plurality of blood pressure sensors 213 and wires (not shown) and electrode pads (not shown) connected to each of the blood pressure sensors 213. The electrode pads are electrically connected to the wires printed on the flexible printed circuit board 202. In FIG. 6, for convenience, each of the blood pressure measuring units 210 includes three blood pressure sensors 213, but the present invention is not limited thereto.

In FIG. 6, a plurality of blood pressure measuring units 210, each having a plurality of blood pressure sensors 213 are physically differentiated, but the present invention is not limited thereto. For example, the blood pressure measuring units 210 may include a plurality of blood pressure sensors formed by dividing the blood pressure sensors disposed in a row into n groups.

FIG. 7 is a flow chart showing a method of measuring blood pressure according to another embodiment of the present invention.

The method of measuring blood pressure according to another embodiment of the present will now be described with reference to FIG. 6.

The plurality of blood pressure sensors 213 formed on the flexible printed circuit board 202 are divided into n groups (S20). Each of the blood pressure measuring units 210, each including a plurality of the blood pressure sensors 213, may be one group among the n groups. Otherwise, the blood pressure sensors 213 are disposed in a row, and divided in to the n groups.

Next, one of the blood pressure sensors 213 that belong to each group is selected as a representative blood pressure sensor 213 (S21). The representative blood pressure sensor 213 may be the blood pressure sensor 213 located in the center of each of the blood pressure sensor groups.

A representative blood pressure sensor 213 that shows the maximum artery pulse is determined by analyzing artery pulses measured by the representative blood pressure sensors 213 (S22).

A blood pressure sensor 213 that shows the maximum artery pulse is determined among the blood pressure sensors belongs to the group to which the representative blood pressure sensor 213 determined in the operation S22 belongs (S23). The blood pressure sensor 213 showing the maximum artery pulse is determined as being positioned on the radial artery.

Blood pressure is measured using the blood pressure sensor 213 determined in the operation S23 (S24).

The method of measuring blood pressure according to the present invention primarily detects a group of the blood pressure sensors on the radial artery and finds the blood pressure sensor located on the radial artery from the blood pressure sensors that belong to a selected group. Thus, the number of artery pulse analysis for finding the blood pressure sensor positioned on the radial artery may be greatly reduced, and thus, the time required for finding the radial artery may be reduced. Also, the sensitivity of finding the radial artery may be increased since many blood pressure sensors may be used.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A blood pressure measuring apparatus comprising:
    a plurality of blood pressure measuring units disposed on a substrate;
    a plurality of optical sensors disposed on the substrate, each optical sensor corresponding to a respective one of the plurality of blood pressure measuring units; and
    a control unit that measures blood pressure by analyzing signals received from at least one of the plurality of optical sensors and at least one of the plurality of blood pressure measuring units,
    wherein each of the plurality of blood pressure measuring units comprises a plurality of blood pressure sensors,
    wherein the plurality of the optical sensors measure optical signals by emitting and receiving light,
    wherein the plurality of blood pressure sensors of the blood pressure measuring unit of the plurality of blood pressure measuring units that corresponds to an optical sensor of the plurality of optical sensors showing a maximum variation of the measured optical signal each measure an artery pulse according to blood pressure, and
    wherein the blood pressure sensor of the plurality of blood pressure sensors of the blood pressure measuring unit used to measure artery pulses that shows a maximum artery pulse is determined, and the determined blood pressure sensor is used to measure blood pressure.

2. The blood pressure measuring apparatus of claim 1, wherein the substrate is a flexible printed circuit board on which wires electrically connected to the plurality of blood pressure sensors and the plurality of optical sensors are formed.

3. The blood pressure measuring apparatus of claim 1, wherein the blood pressure sensor is a piezoresistor.

4. The blood pressure measuring apparatus of claim 1, wherein each of the plurality of optical sensors comprises a light emitting unit and a light receiving unit, wherein the light emitting unit and the light receiving unit are respectively disposed on both sides of corresponding blood pressure measuring units.

\* \* \* \* \*